US008864952B2

(12) United States Patent
Sinha et al.

(10) Patent No.: US 8,864,952 B2
(45) Date of Patent: Oct. 21, 2014

(54) APPARATUSES AND METHODS FOR SEPARATING PARAFFIN ISOMERIZATION-ZONE EFFLUENTS

(71) Applicant: UOP LLC, Des Plaines, IL (US)

(72) Inventors: Anurag Sinha, Haryana (IN); Manoj Kumar, Haryana (IN); David James Shecterle, Arlington Heights, IL (US); Douglas A. Becci, Carol Stream, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/715,813

(22) Filed: Dec. 14, 2012

(65) Prior Publication Data

US 2014/0171717 A1 Jun. 19, 2014

(51) Int. Cl.
*B01D 3/14* (2006.01)
*B01D 3/16* (2006.01)
*B01D 3/32* (2006.01)
*C07C 7/04* (2006.01)

(52) U.S. Cl.
CPC .. *B01D 3/324* (2013.01); *C07C 7/04* (2013.01)
USPC .............................. 203/86; 203/71; 585/802

(58) Field of Classification Search
CPC ................................... B01D 3/14; B01D 3/16
See application file for complete search history.

(56) References Cited

U.S. PATENT DOCUMENTS

| 2,974,182 | A | 3/1961 | Van Pool et al. |
| 3,041,843 | A | 7/1962 | Swearingen et al. |
| 4,082,502 | A | 4/1978 | Von Der Eltz et al. |
| 4,324,936 | A | 4/1982 | Mikulicz |
| 5,806,339 | A | 9/1998 | Manley |
| 7,946,123 | B2 | 5/2011 | Tolbert, Jr. et al. |
| 2008/0081933 | A1* | 4/2008 | Bastings et al. ............. 568/858 |
| 2011/0011723 | A1* | 1/2011 | Bastings et al. ............. 202/153 |

FOREIGN PATENT DOCUMENTS

WO 2007144360 A2 12/2007

* cited by examiner

*Primary Examiner* — Tam M Nguyen
(74) *Attorney, Agent, or Firm* — Maryann Maas

(57) ABSTRACT

Embodiments of apparatuses and methods for separating a paraffin isomerization-zone effluent are provided. In one example, an apparatus comprises a DIB column configured for fractionating the paraffin isomerization-zone effluent to form a branched $C_4$ hydrocarbon-rich stream. The DIB column comprises a vessel. The vessel comprises a cylindrical wall that extends vertically and that encloses an internal cylindrical volume having a lower portion extending to an upper portion. An internal swage is disposed in the lower portion of the internal cylindrical volume. A plurality of fractionation trays includes an upper fractionation tray that is disposed in the internal cylindrical volume above the internal swage and a lower fractionation tray that is disposed in the internal swage. The lower fractionation tray has a smaller diameter than the upper fractionation tray.

17 Claims, 3 Drawing Sheets

APPARATUSES AND METHODS FOR SEPARATING PARAFFIN ISOMERIZATION-ZONE EFFLUENTS

TECHNICAL FIELD

The technical field relates generally to apparatuses and methods for separating hydrocarbons, and more particularly relates to apparatuses and methods for separating an effluent containing paraffin isomers from a paraffin isomerization-zone.

BACKGROUND

Isomerization processes are widely used by many refiners to rearrange the molecular structure of straight chain paraffinic hydrocarbons to more highly branched hydrocarbons that generally have higher octane ratings. One such process rearranges normal butane (n-butane) to isobutane in a paraffin isomerization-zone. The isomerization process proceeds toward a thermodynamic equilibrium in which the effluent (isomerate) still contains a substantial concentration of n-butane, typically in the range of a mole ratio of isobutane to n-butane of from about 1.2:1 to about 2:1. Downstream from the paraffin isomerization-zone, the effluent is separated in a deisobutanizer (DIB) column to form an isobutane product, usually having a purity of at least about 80 mole % and up to about 99 mole % isobutane. The DIB column is configured as a fractional distillation column with a plurality of vertically aligned and spaced apart fractionation trays that effectively act as vapor-liquid contacting devices for fractionating the effluent.

As the boiling points of n-butane and isobutane are relatively close and a relatively pure isobutane product is desired, DIB columns typically operate with a high reflux ratio to help drive the vapor fractions of the effluent up through the DIB column contacting the descending liquid fractions of the effluent to effectively separate the isobutane product. Unfortunately, in efforts to be more energy efficient, some DIB columns are designed with significantly lower reboiling duties in the lower portion of the column compared to the upper portion of the column, e.g., ratio of the reboiling duties of the lower portion relative to the upper portion of the column of from about 1:9 to about 1:10. As such, significantly less vapor is generated in the lower portion of the DIB column than in the upper portion of the column. This can result in lower vapor velocities and flow of liquid through the holes on the fractionation trays called weeping, leading to inefficient separation of the paraffin isomerization-zone effluent and a lower purity isobutane product.

Accordingly, it is desirable to provide apparatuses and methods for separating paraffin isomerization-zone effluents with improved vapor velocity and reduced weeping in DIB columns for efficient separation of isobutane from the effluent. Furthermore, other desirable features and characteristics of the present invention will become apparent from the subsequent detailed description and the appended claims, taken in conjunction with the accompanying drawings and this background.

BRIEF SUMMARY

Apparatuses and methods for separating paraffin isomerization-zone effluents are provided herein. In accordance with an exemplary embodiment, an apparatus for separating an isomerization-zone effluent comprises a DIB column. The DIB column is configured for fractionating the paraffin isomerization-zone effluent to form a branched $C_4$ hydrocarbon-rich stream. The DIB column comprises a vessel. The vessel comprises a cylindrical wall that extends vertically and that encloses an internal cylindrical volume having a lower portion extending to an upper portion. An internal swage is disposed in the lower portion of the internal cylindrical volume. A plurality of fractionation trays includes an upper fractionation tray that is disposed in the internal cylindrical volume above the internal swage and a lower fractionation tray that is disposed in the internal swage. The lower fractionation tray has a smaller diameter than the upper fractionation tray.

In accordance with another exemplary embodiment, an apparatus for separating an isomerization-zone effluent is provided. The apparatus comprises a DIB column that is configured for separating the paraffin isomerization-zone effluent into vapor and liquid fractions to form a branched $C_4$ hydrocarbon-rich stream and a $C_4^+$ hydrocarbon-containing stream. The DIB column comprises a vessel. The vessel comprises a cylindrical wall that extends vertically and that encloses an internal cylindrical volume having a lower portion extending to an upper portion. An internal swage is disposed in the lower portion. A plurality of fractionation trays includes an upper fractionation tray that is disposed in the internal cylindrical volume above the internal swage and a lower fractionation tray that is disposed in the internal swage. The lower fractionation tray has less bubbling area than the upper fractionation tray. A lower reboiler is in fluid communication with the DIB column to receive a portion of the $C_4^+$ hydrocarbon-containing stream. The lower reboiler is configured to heat the portion of the $C_4^+$ hydrocarbon-containing stream to form a first reboiler outlet stream that is returned to the DIB column below the internal swage. An upper reboiler is in fluid communication with the DIB column to receive a liquid fraction of the paraffin isomerization-zone effluent. The upper reboiler is configured to heat the liquid fraction to form a second reboiler outlet stream that is returned to the DIB column above the internal swage. A heat pump compressor is configured to receive a vapor portion of the branched $C_4$ hydrocarbon-rich stream and to form a compressed branched $C_4$ hydrocarbon-rich stream. The upper reboiler comprises an upper heat exchanger that is in fluid communication with the heat pump compressor to receive the compressed branched $C_4$ hydrocarbon-rich stream for indirect heat exchange with the liquid fraction to form the second reboiler outlet stream.

In accordance with another exemplary embodiment, a method for separating a paraffin isomerization-zone effluent is provided. The method comprises the steps of fractionating the paraffin isomerization-zone effluent to form a branched $C_4$ hydrocarbon-rich stream. Fractionating the paraffin isomerization-zone effluent comprises forming a first vapor-liquid contacting zone with first vapor and liquid fractions of the paraffin isomerization-zone effluent along a lower fractionation trayed section that is disposed in an internal swage in a lower portion of a DIB column. A second vapor-liquid contacting zone is formed with second vapor and liquid fractions of the paraffin isomerization-zone effluent along an upper fractionation trayed section that is disposed in the DIB column above the internal swage. The lower fractionation trayed section has a smaller diameter than the upper fractionation trayed section.

BRIEF DESCRIPTION OF THE DRAWINGS

The various embodiments will hereinafter be described in conjunction with the following drawing figures, wherein like numerals denote like elements, and wherein.

DETAILED DESCRIPTION

The following Detailed Description is merely exemplary in nature and is not intended to limit the various embodiments or the application and uses thereof. Furthermore, there is no intention to be bound by any theory presented in the preceding background or the following detailed description.

Various embodiments contemplated herein relate to apparatuses and methods for separating a paraffin isomerization-zone effluent that contains paraffin isomers including n-butane and isobutane. Unlike the prior art, the exemplary embodiments taught herein employ a DIB column that is configured to receive the paraffin isomerization-zone effluent and that includes an internal swage disposed in a lower portion of an internal cylindrical volume of the DIB column. In an exemplary embodiment, the internal swage is configured as an open ended shaped tube with a flared tubular section that is disposed adjacent to the cylindrical wall of the DIB column and a narrower straight tubular section that extends downward from the flared tubular section coaxially with the lower portion of the DIB column. The internal swage effectively reduces the diameter of the lower portion of the DIB column through which vapor generated in the lower portion of the DIB column can rise through into the upper portion of the column.

The DIB column includes a plurality of fractionation trays including an upper fractionation tray that is disposed in the internal cylindrical volume above the internal swage and a lower fractionation tray that is disposed in the internal swage. In an exemplary embodiment, the fractionation trays are configured as perforated horizontal decking, e.g., flat plates each with a number of holes formed therethrough, defining a bubbling or active area of the tray through which vapor can rise through the holes in the horizontal decking. Because the lower fractionation tray is disposed in the internal swage, it has a smaller diameter than the upper fractionation tray and therefore, a correspondingly smaller bubbling area than the upper fractionation tray. As such, in DIB columns where less vapor is generated in the lower portion of the DIB column than in the upper portion of the column, the smaller bubbling area of the lower fractionation tray requires less vapor traffic to achieve desirable vapor velocities to reduce or prevent liquid from flowing down through the holes on the fractionation tray, thereby reducing or preventing weeping in the DIB column.

Figure 1:
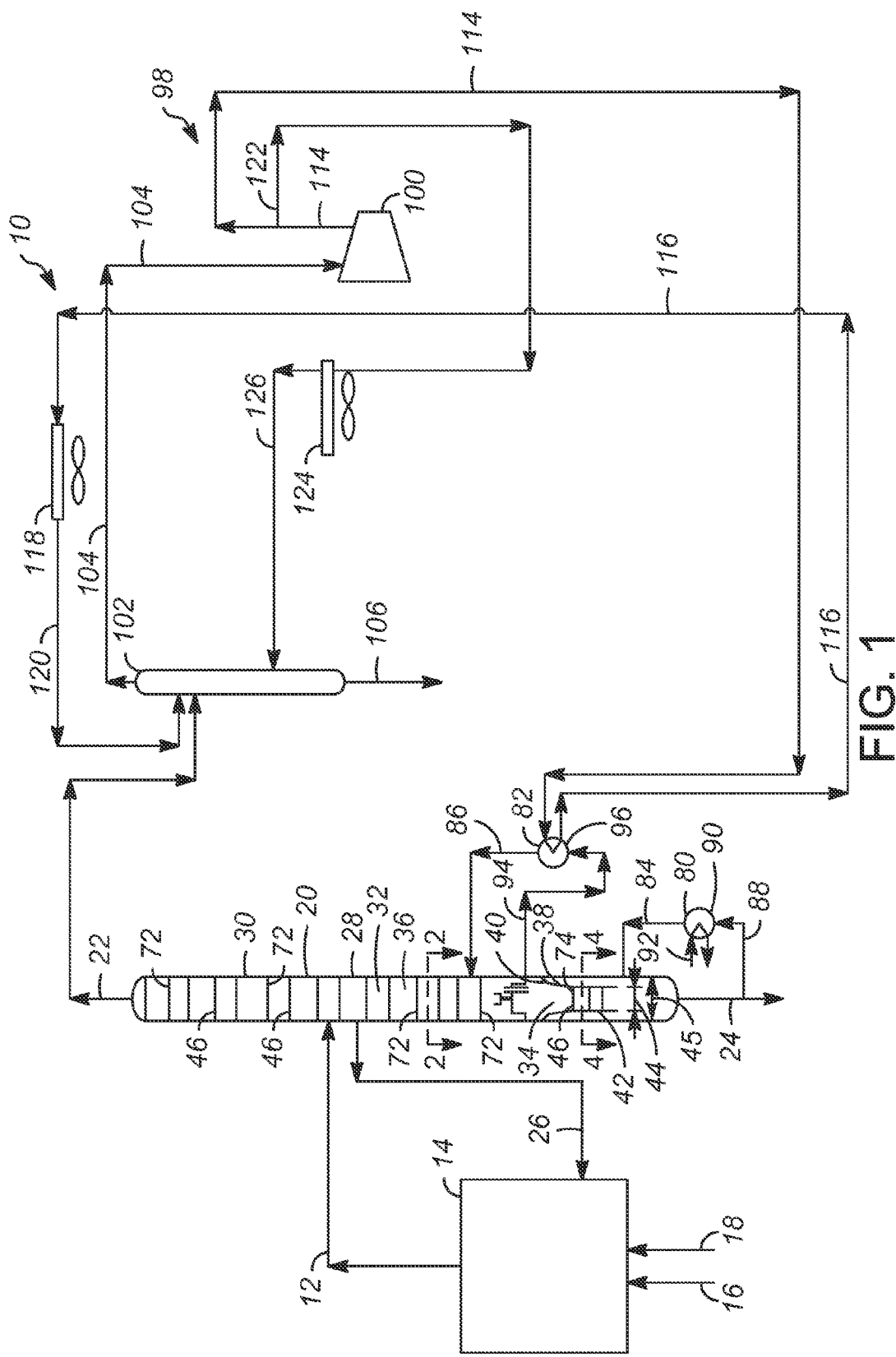
FIG. 1 schematically illustrates an apparatus and method including a DIB column for separating an isomerization-zone effluent in accordance with an exemplary embodiment.

Referring to FIG. 1, a schematic depiction of an apparatus 10 for separating a paraffin isomerization-zone effluent 12 in accordance with an exemplary embodiment is provided. As illustrated, the paraffin isomerization-zone effluent 12 is formed in a paraffin isomerization-zone 14. As used herein, the term "zone" refers to an area including one or more equipment items and/or one or more sub-zones. Equipment items can include one or more reactors or reactor vessels (e.g., reaction zone), heaters, exchangers, pipes, pumps, compressors, and controllers. Additionally, an equipment item, such as a reactor, dryer, or vessel, can further include one or more zones or sub-zones.

A paraffin feed stream 16 and a hydrogen-containing gas stream 18 are introduced to the paraffin isomerization-zone 14. In an exemplary embodiment, the paraffin feed stream 16 is rich in $C_4$ hydrocarbons, such as n-butane and may also contain relatively small amounts of isobutane, pentane, and heavier materials (e.g., $C_6^+$ hydrocarbons). As used herein, $C_X$ means hydrocarbon molecules that have "X" number of carbon atoms, $C_X^+$ means hydrocarbon molecules that have "X" and more than "X" number of carbon atoms, and $C_X^-$ means hydrocarbon molecules that have "X" and less than "X" number of carbon atoms.

In an exemplary embodiment, the paraffin isomerization-zone 14 includes various sub-zones including a reaction sub-zone and a scrubbing sub-zone. The reaction sub-zone contains a chloride-promoted isomerization catalyst. Non-limiting examples of the isomerization catalyst include alumina catalyst, platinum aluminum catalyst, and the like that can be chlorinated. The chloride-promoted isomerization catalyst in the presence the hydrogen-containing gas stream 18 at isomerization conditions is effective to isomerize the normal paraffins to branched paraffins, e.g., n-butane to branched or isobutane. In an exemplary embodiment, the isomerization conditions include a reactor temperature of from about 90 to about 210° C. An effluent formed in the reaction sub-zone is scrubbed in the scrubbing sub-zone to remove HCl and form the paraffin isomerization-zone effluent 12. In an exemplary embodiment, the paraffin isomerization-zone effluent 12 comprises isobutane, n-butane, and other $C_5^+$ hydrocarbons.

The paraffin isomerization-zone effluent 12 is passed along to the apparatus 10 and introduced to a DIB column 20. In an exemplary embodiment, the DIB column 20 is configured to separate the paraffin isomerization-zone effluent 12 into vapor and liquid fractions to form a branched $C_4$ hydrocarbon-rich stream 22 that is rich in isobutane, a $C_4^+$ hydrocarbon-containing stream 24 that contains most of the $C_5/C_6$ hydrocarbons contained in stream 12 and some $C_4$ hydrocarbons, and a normal $C_4$ hydrocarbon-rich stream 26 that is rich in n-butane. As illustrated, the normal $C_4$ hydrocarbon-rich stream 26 is returned to the paraffin isomerization-zone 14 and combined with the paraffin feed stream 16 for introduction to the reaction sub-zone as discussed above.

The DIB column 20 comprises a vessel 28 including a cylindrical wall 30 that extends vertically and encloses an internal cylindrical volume 32 having a lower portion 34 extending to an upper portion 36. An internal swage 38 is disposed in the lower portion 34. As illustrated, the internal swage 38 is configured as an open ended shaped tube with a flared tubular section 40 that is sealed against the cylindrical wall 30 of the DIB column 20 and a narrower straight tubular section 42 that extends downward from the flared tubular section 40 coaxially with the lower portion 34 of the DIB column 20. The internal swage 38 effectively reduces the diameter of the lower portion 34 of the DIB column 20 through which vapor generated in the lower portion 34 of the DIB column 20 can rise through into the upper portion 36 of the DIB column 20. In particular and as illustrated, the narrower straight tubular section 42 has an internal diameter (indicated by arrows 44) that is substantially less than an internal diameter (indicated by double headed arrow 45) of the vessel 28. In an exemplary embodiment, a diameter ratio of the internal diameter 44 of the narrower straight tubular section 42 to the internal diameter 45 of the vessel 28 is from about 0.1 to about 0.9, such as from about 0.15 to about 0.6.

Figure 2:
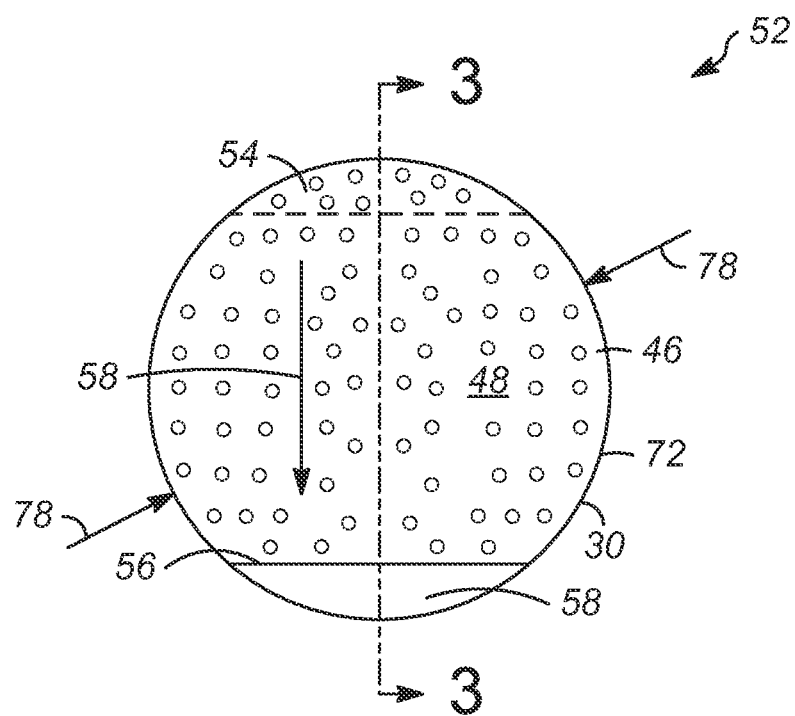
FIG. 2 is a sectional view of the DIB column depicted in FIG. 1 along line 2-2.
Figure 3:
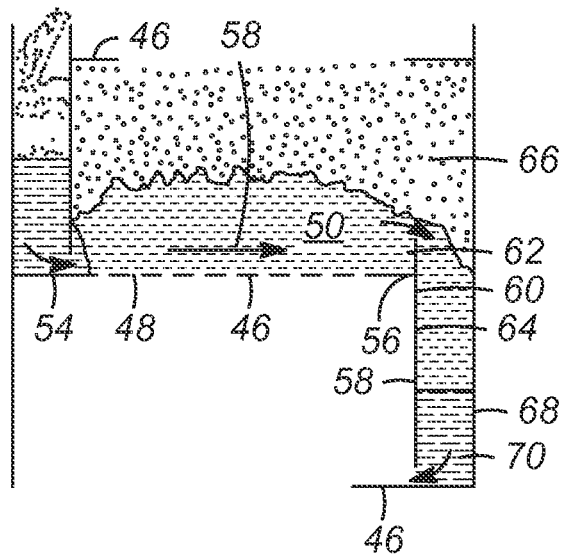
FIG. 3 is a sectional view of the DIB column depicted in FIG. 2 along line 3-3.

The DIB column 20 has a plurality of fractionation trays 46 that are vertically aligned and spaced apart from each other in the internal cylindrical volume 32 for fractional distillation of the paraffin isomerization-zone effluent 12. Referring also to FIGS. 2-3, the fractionation trays 46 each comprise a perforated horizontal decking 48 that carries a vapor-liquid froth 50 comprising a vapor-liquid equilibrium of vapor and liquid fractions of the paraffin isomerization-zone effluent 12. In general and as is well known in fractional distillation, the vapor-liquid froth 50 carried across a particular fractionation tray 46 will have a distinct composition corresponding to the relative volatility of the components contained in the vapor-liquid froth 50 and the vapor-liquid equilibrium of those components at the particular temperature and pressure about the fractionation tray 46. As illustrated, the fractionation trays 46 are configured as a full diameter single-pass cross flow trays 52, which means that the vapor-liquid froth 50 passes from an inlet side 54 to an outlet side 56 of the perforated horizontal decking 48 in a single direction (indicated by single headed arrow 58) before entering an outlet downcomer 58 and flowing onto the next lower tray. While the fractionation trays 46 are shown as single-pass cross flow trays 52 for illustrative purposes only, it is to be understood that the fractionation trays 46 may be similarly or independently configured as any alternatively configured fractionation tray, such as, for example, a double pass tray, a multi-downcomer (MD) tray, or the like as are well known in the art.

The outlet downcomer 58 includes a downcomer end wall 60 that extends above the perforated horizontal decking 48 to form an outlet weir 62 for removing a portion of the vapor-liquid froth 50 from the perforated horizontal decking 48. The downcomer end wall 60 extends below the perforated horizontal decking 48 to form an outlet apron 64 that confines a downcomer volume to allow vapor 66 entrained in the vapor-liquid froth 50 to escape, leaving essentially only a liquid fraction 68 in a liquid dominant section 70 of the outlet downcomer 58. The bottom edge of the downcomer end wall 60 is a short distance from the next lower fractionation tray 46 to allow the liquid fraction 68 to flow through and onto the next lower fractionation tray 46.

Figure 4:
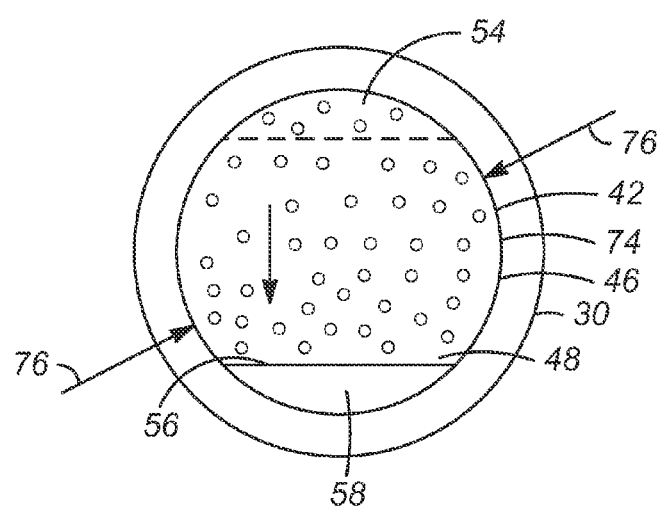
FIG. 4 is a sectional view of the DIB column depicted in FIG. 1 along line 4-4.

Referring to FIGS. 1-2 and 4, the plurality of fractionation trays 46 include upper fractionation trays 72 that are disposed above the internal swage 38 and lower fractionation trays 74 that are disposed in the internal swage 38. As illustrated, the upper fractionation trays 72 are disposed immediately adjacent to the cylindrical wall 30 and the lower fractionation trays 74 are disposed in the narrower straight tubular section 42 of the internal swage 38 but may also be positioned in the flared tubular section 40 if desired. Because the lower fractionation trays 74 are disposed in the internal swage 38, they have a smaller diameter (indicated by single headed arrows 76) than the diameter (indicated by single headed arrows 78) of the upper fractionation trays 72. As such, the lower fractionation trays 74 have a correspondingly smaller bubbling area than the upper fractionation trays 72. In an exemplary embodiment, a diameter ratio defined by the diameter 76 of the lower fractionation trays 74 divided by the diameter 78 of the upper fractionation trays 72 is from about 0.1 to about 0.9, such as from about 0.15 to about 0.6. In another exemplary embodiment, a bubbling area ratio defined by the area of the perforated horizontal decking 48 of the lower fractionation trays 74 divided by the area of the perforated horizontal decking 48 of the upper fractionation trays 72 is from about 0.01 to about 0.81, such as from about 0.1 to about 0.6.

Referring to FIG. 1, the apparatus 10 further comprises a lower reboiler 80 (e.g., bottom reboiler) and an upper reboiler 82 (e.g., sidedraw reboiler) for producing a lower reboiler outlet stream 84 and an upper reboiler outlet stream 86 that are directed back to the DIB column 20 below and above the internal swage 38, respectively. In particular and as illustrated, a portion 88 of the $C_4^+$ hydrocarbon-containing stream 24 is passed along to a heat exchanger 90 of the lower reboiler 80. In an exemplary embodiment, steam 92 is passed through the heat exchanger 90 for indirect heat exchange with the portion 88 to produce the lower reboiler outlet stream 84. In one example, the lower reboiler 80 forms the lower reboiler outlet stream 84 having a temperature of from about 70 to about 90° C. In one embodiment, the lower fractionation trays 74 are exposed to vapors rising from the lower reboiler outlet stream 84 and are at a temperature of from about 40 to about 90° C.

A liquid fraction 94 of the paraffin isomerization-zone effluent 12 is passed along to a heat exchanger 96 of the upper reboiler 82. The upper reboiler 82 is configured to heat the liquid fraction 94 to form the upper reboiler outlet stream 86. In an exemplary embodiment, the upper reboiler 82 forms the upper reboiler outlet stream 86 having a temperature of from about 40 to about 60° C. In one embodiment, the upper fractionation trays 72 are exposed to vapors rising from the upper reboiler outlet stream 86 and are at a temperature of from about 20 to about 60° C.

In an exemplary embodiment, the upper reboiler 82 cooperates with a heat pump arrangement 98 comprising a heat pump compressor 100 for indirect heat exchange with the liquid fraction 94 to form the upper reboiler outlet stream 86. As illustrated, the branched $C_4$ hydrocarbon-rich stream 22 is removed from the DIB column 20 as an overhead stream and is passed along to a heat pump compressor suction drum 102. The heat pump compressor suction drum 102 effectively acts as an overhead receiver that separates the branched $C_4$ hydrocarbon-rich stream 22 into a vapor portion 104 and a liquid portion 106 that are both rich in branched $C_4$ hydrocarbon, e.g., isobutane. The liquid portion 106 is removed from the heat pump compressor suction drum 102 as an isobutane-rich product stream.

The vapor portion 104 is removed from the heat pump compressor suction drum 102 and is introduced to the heat pump compressor 100. The heat pump compressor 100 is configured to compress the vapor portion 104 to form a compressed branched $C_4$ hydrocarbon-rich stream 114. In an exemplary embodiment, the heat pump compressor 100 forms the compressed branched $C_4$ hydrocarbon-rich stream 114 having a pressure of from about 600 to about 900 kPa gauge and a temperature of from about 50 to about 75° C.

The compressed branched $C_4$ hydrocarbon-rich stream 114 is directed to the heat exchanger 96 of the upper reboiler 82 for indirect heat exchange with the liquid fraction 94 to form the upper reboiler outlet stream 86 as discussed above and a first partially cooled compressed branched $C_4$ hydrocarbon-rich stream 116. In an exemplary embodiment, the first partially cooled compressed branched $C_4$ hydrocarbon-rich stream 116 has a temperature of from about 40 to about 65° C. As illustrated, the first partially cooled compressed branched $C_4$ hydrocarbon-rich stream 116 is passed through a condenser 118 to form a second partially cooled compressed branched $C_4$ hydrocarbon-rich stream 120 that is introduced to the heat pump compressor suction drum 102. In an exemplary embodiment, the condenser 118 forms the second partially cooled compressed branched $C_4$ hydrocarbon-rich stream 120 having a temperature of from about 30 to about 50° C. Optionally, downstream from the heat pump compressor 100, a portion 122 of the compressed branched $C_4$ hydrocarbon-rich stream 114 may be directed through a condenser 124 to form a third partially cooled compressed branched $C_4$ hydrocarbon-rich stream 126 that is introduced to the heat pump compressor suction drum 102. In an exemplary embodiment, the condenser 124 forms the partially cooled compressed branched $C_4$ hydrocarbon-rich stream 126 having a temperature of from about 30 to about 50° C.

In an exemplary embodiment, use of the heat pump arrangement 98 along with the lower and upper reboilers 80 and 82 reduces the steam requirements for operating the DIB column 20 at a relatively high reflux ratio. Further, because the lower fractionation trays 74 have a smaller bubbling area compared to the upper fractionation trays 72, the DIB column 20 may be operated with a lower reboiler duty in the lower portion 34 of the DIB column 20 compared to the reboiler duty in the upper portion 36 of the DIB column while still achieving desirable vapor velocities to reduce or prevent liquid from draining through the holes on the fractionation trays 46, thereby reducing or preventing weeping in the DIB column 20.

Accordingly, apparatuses and methods for separating a paraffin isomerization-zone effluent have been described. Unlike the prior art, the exemplary embodiments taught herein employ a DIB column that is configured to receive the paraffin isomerization-zone effluent and that includes an internal swage disposed in a lower portion of the internal cylindrical volume of the DIB column. The internal swage effectively reduces the diameter of the lower portion of the DIB column through which vapor generated in the lower portion of the DIB column can rise through into the upper portion of the column. The DIB column includes a plurality of fractionation trays including an upper fractionation tray that is disposed in the internal cylindrical volume above the internal swage and a lower fractionation tray that is disposed in the internal swage. Because the lower fractionation tray is disposed in the internal swage, it has a smaller diameter than the upper fractionation tray and therefore, a correspondingly smaller bubbling area than the upper fractionation tray. As such, less vapor traffic is required in the lower portion of the DIB column to achieve desirable vapor velocities to reduce or prevent weeping in the DIB column.

While at least one exemplary embodiment has been presented in the foregoing detailed description of the disclosure, it should be appreciated that a vast number of variations exist. It should be also appreciated that the exemplary embodiment or exemplary embodiments are only examples, and are not intended to limit the scope, applicability, or configuration of the disclosure in any way. Rather, the foregoing detailed description will provide those skilled in the art with a convenient road map for implementing an exemplary embodiment of the disclosure. It being understood that various changes may be made in the function and arrangement of elements described in an exemplary embodiment without departing from the scope of the disclosure as set forth in the appended claims.

What is claimed is:

1. An apparatus for separating a paraffin isomerization-zone effluent, the apparatus comprising:
    a DIB column that is configured for fractionating the paraffin isomerization-zone effluent to form a branched $C_4$ hydrocarbon-rich stream, the DIB column comprising:
        a vessel comprising a cylindrical wall that extends vertically and that encloses an internal cylindrical volume having a lower portion extending to an upper portion;
        an internal swage that is disposed in the lower portion; and
        a plurality of fractionation trays including an upper fractionation tray that is disposed in the internal cylindrical volume above the internal swage and a lower fractionation tray that is disposed in the internal swage and that has a smaller diameter than the upper fractionation tray.

2. The apparatus of claim 1, wherein the lower fractionation tray has a first diameter and the upper fractionation tray has a second diameter, and wherein the first diameter divided by the second diameter defines a diameter ratio of from about 0.1 to about 0.9.

3. The apparatus of claim 2, wherein the diameter ratio is from about 0.15 to about 0.6.

4. The apparatus of claim 1, further comprising a lower reboiler in fluid communication with the DIB column to receive a first liquid fraction of the paraffin isomerization-zone effluent, and wherein the lower reboiler is configured to heat the first liquid fraction to form a first reboiler outlet stream that is returned to the DIB column below the internal swage.

5. The apparatus of claim 4, wherein the lower reboiler is configured to form the first reboiler outlet stream having a temperature of from about 70 to about 90° C.

6. The apparatus of claim 1, further comprising an upper reboiler in fluid communication with the DIB column to receive a second liquid fraction of the paraffin isomerization-zone effluent, and wherein the upper reboiler is configured to heat the second liquid fraction to form a second reboiler outlet stream that is returned to the DIB column above the internal swage.

7. The apparatus of claim 6, wherein the upper reboiler is configured to form the second reboiler outlet stream having a temperature of from about 40 to about 60° C.

8. The apparatus of claim 6, further comprising a heat pump compressor that is configured to receive a vapor portion of the branched $C_4$ hydrocarbon-rich stream and to form a compressed branched $C_4$ hydrocarbon-rich stream, wherein the upper reboiler comprises an upper heat exchanger that is in fluid communication with the heat pump compressor to receive the compressed branched $C_4$ hydrocarbon-rich stream for indirect heat exchange with the second liquid fraction to form the second reboiler outlet stream.

9. The apparatus of claim 8, wherein the heat pump compressor is configured to form the compressed branched $C_4$ hydrocarbon-rich stream having a pressure of from about 600 to about 900 kPa gauge.

10. The apparatus of claim 8, wherein the heat pump compressor is configured to form the compressed branched $C_4$ hydrocarbon-rich stream having a temperature of from about 50 to about 75° C.

11. The apparatus of claim 8, further comprising a heat pump compressor suction drum in fluid communication with the DIB column to receive the branched $C_4$ hydrocarbon-rich stream, wherein the heat pump compressor suction drum is configured to separate the branched $C_4$ hydrocarbon-rich stream into the vapor portion and a liquid portion of the branched $C_4$ hydrocarbon-rich stream, and wherein the heat pump compressor is in fluid communication with the heat pump compressor suction drum to receive the vapor portion of the branched $C_4$ hydrocarbon-rich stream.

12. The apparatus of claim 11, wherein the heat pump compressor suction drum is in fluid communication with the heat pump compressor to receive a portion of the compressed branched $C_4$ hydrocarbon-rich stream.

13. The apparatus of claim 12, further comprising a condenser that is configured to cool the portion of the compressed branched $C_4$ hydrocarbon-rich stream prior to being introduced to the heat pump compressor suction drum.

14. The apparatus of claim 13, wherein the condenser is configured to cool the compressed branched $C_4$ hydrocarbon-rich stream to a temperature of from about 30 to about 50° C. prior to being introduced to the heat pump compressor suction drum.

15. An apparatus for separating a paraffin isomerization-zone effluent, the apparatus comprising:
- a DIB column that is configured for separating the paraffin isomerization-zone effluent into vapor and liquid fractions to form a branched $C_4$ hydrocarbon-rich stream and a $C_4^+$ hydrocarbon-containing stream, the DIB column comprising:
  - a vessel comprising a cylindrical wall that extends vertically and that encloses an internal cylindrical volume having a lower portion extending to an upper portion;
  - an internal swage that is disposed in the lower portion; and
  - a plurality of fractionation trays including an upper fractionation tray that is disposed in the internal cylindrical volume above the internal swage and a lower fractionation tray that is disposed in the internal swage and that has less bubbling area than the upper fractionation tray;
- a lower reboiler in fluid communication with the DIB column to receive a portion of the $C_4+$ hydrocarbon-containing stream and configured to heat the portion to form a first reboiler outlet stream that is returned to the DIB column below the internal swage;
- an upper reboiler in fluid communication with the DIB column to receive a liquid fraction of the paraffin isomerization-zone effluent and configured to heat the liquid fraction to form a second reboiler outlet stream that is returned to the DIB column above the internal swage; and
- a heat pump compressor that is configured to receive a vapor portion of the branched $C_4$ hydrocarbon-rich stream and to form a compressed branched $C_4$ hydrocarbon-rich stream, wherein the upper reboiler comprises an upper heat exchanger that is in fluid communication with the heat pump compressor to receive the compressed branched $C_4$ hydrocarbon-rich stream for indirect heat exchange with the liquid fraction to form the second reboiler outlet stream.

16. The apparatus of claim 15, wherein the lower reboiler comprises a lower heat exchanger that is configured to receive steam for indirect heat exchange with the portion of the $C_4+$ hydrocarbon-containing stream to form the first reboiler outlet stream.

17. The apparatus of claim 15, wherein the lower fractionation tray has a first bubbling area and the upper fractionation tray has a second bubbling area, and wherein the first bubbling area divided by the second bubbling area defines a bubbling area ratio of from about 0.01 to about 0.81.

* * * * *